ус007501363В2

United States Patent
Dharmadhikary et al.

(10) Patent No.: US 7,501,363 B2
(45) Date of Patent: Mar. 10, 2009

(54) ETHYLENE OXIDE STERILIZABLE, LOW COST NONWOVEN LAMINATES WITH HIGH WET PEEL STRENGTH AND IMPROVED BARRIER PROPERTIES

(75) Inventors: Rahul K. Dharmadhikary, South Windsor, CT (US); Alexander M. Kronfeld, Avon, CT (US); Patrick Z. Chen, Simsbury, CT (US); Gordon D. Meikle, Duns (GB)

(73) Assignee: The Boeing Company, Chicago, IL (US)

( * ) Notice: Subject to any disclaimer, the term of this patent is extended or adjusted under 35 U.S.C. 154(b) by 185 days.

(21) Appl. No.: 10/535,498

(22) PCT Filed: Dec. 12, 2003

(86) PCT No.: PCT/US03/39549

§ 371 (c)(1),
(2), (4) Date: May 18, 2005

(87) PCT Pub. No.: WO2004/054801

PCT Pub. Date: Jul. 1, 2004

(65) Prior Publication Data

US 2006/0052025 A1    Mar. 9, 2006

(51) Int. Cl.
*B32B 27/12* (2006.01)
*B32B 27/00* (2006.01)
(52) U.S. Cl. .................. 442/398; 442/394; 428/424.8
(58) Field of Classification Search ................ 442/394, 442/398, 361, 400, 401
See application file for complete search history.

(56) References Cited

U.S. PATENT DOCUMENTS

| 3,809,077 | A | 5/1974 | Hansen |
| 4,695,334 | A | 9/1987 | Mays |
| 6,394,095 | B1 | 5/2002 | Idman et al. |
| 6,511,927 | B1 | 1/2003 | Ellis et al. |
| 6,564,803 | B2 | 5/2003 | Lofgren |
| 6,615,837 | B1 | 9/2003 | Griesbach, III |
| 6,624,100 | B1 | 9/2003 | Pike |
| 6,638,605 | B1 | 10/2003 | Ankuda, Jr. et al. |
| 2004/0091752 | A1* | 5/2004 | Morman et al. ............. 428/910 |
| 2004/0123939 | A1* | 7/2004 | Griesbach et al. ........... 156/164 |

FOREIGN PATENT DOCUMENTS

WO    0006381 A1    2/2000

OTHER PUBLICATIONS

Cocuzza, Carl, "An Update on Hot Melt Adhesive Fiberization", Adhesives Age, Feb. 1994, Argus Inc., Atlanta, Georgia.

* cited by examiner

*Primary Examiner*—Lynda Salvatore
(74) *Attorney, Agent, or Firm*—Ostrager Chong Flaherty & Broitman P.C.

(57) ABSTRACT

Nonwoven laminate products having improved wet peel strength after aging and ethylene oxide sterilization, and improved drape and softness, which are suitable for medical, surgical and hygienic applications, are produced by laminating one or more nonwoven substrates on one or both sides of a cast film. The cast film is produced using conventional extrusion processes, such as co-extrusion. Multiple extruders are used to process and melt different polymers and then specially designed selector plugs and feed-blocks are used to combine the different polymers into different layers to form a multiple layer structure such as A-B, A-B-A, A-B-C, A-B-B-A, etc.

9 Claims, 3 Drawing Sheets

ETHYLENE OXIDE STERILIZABLE, LOW COST NONWOVEN LAMINATES WITH HIGH WET PEEL STRENGTH AND IMPROVED BARRIER PROPERTIES

FIELD OF INVENTION

This invention generally relates to a composite laminate structure for a disposable nonwoven product suitable for use in medical or other hygienic applications and, more particularly, to a low cost nonwoven laminate having improved wet peel strength after aging and ethylene oxide (or "EtO") sterilization, and improved drape and softness.

BACKGROUND OF INVENTION

Nonwoven fabrics and laminates have many applications in the medical and hygienic field. For example, nonwoven laminates may be constructed for applications such as surgical caps, gowns or patient drapes, medical table covers, isolation gowns, scrub apparel or for other protective apparel, among others. In these applications, it is desirable to have a nonwoven laminate product that not only provides comfort (i.e., softness) and good ability to drape as desired (i.e., flexibility), but is also capable of withstanding both processing and in-use conditions. In particular, a nonwoven laminate product sufficient for medical applications should: (i) provide blood, bacteria and viral barrier properties; (ii) be absorbent or repellent (depending on end-use application); and (iii) maintain its integrity (i.e., it should not delaminate) in a wet state, for example, after soaking in bodily fluids such as sweat, urine or blood.

Before use in a medical application, such nonwoven laminates are typically wound on a roll and shipped to a manufacturer, who converts the laminate into the end product, sterilizes the end product using steam, gamma radiation or EtO sterilization, and places the sterilized end product into a plastic pouch. Therefore, it is also desirable for such nonwoven laminates to be constructed to withstand the handling, aging and sterilization required for nonwoven products having medical application without degradation.

To achieve the foregoing properties, many products have been developed comprising multiple thermally bonded nonwoven layers. For example, U.S. Pat. No. 4,695,334 to Mays, which is hereby incorporated by reference, discloses a multiple layer plastic film that is fused or thermally bonded to at least one layer of conjugate fibers having a low melting sheath and a high melting core. The sheaths of the conjugate fibers are fuse bonded to the plastic film at a temperature below the melt temperature of the cores of the conjugate fibers so that the cores retain their initial fiber-like integrity. Other commercially available products utilize alternative methods for bonding a plastic film layer to a fiber layer, such as ultrasonic bonding, adhesive bonding, or thermal spot bonding. It is also known that the Corona treatment improves a fabric's dry peel strength (Butler, T. I. and Veazy, E. W., Film Extrusion Manual: Process, Materials, Properties, 1992, TAPPI Press, Atlanta, pages 363-416).

It has been found, however, that some products exhibit substantially reduced wet peel strengths after aging and EtO sterilization. This may result from migration of adhesive from the interface between the film and fiber layers to the fiber layers when the nonwoven is in roll form, or from the temperature and humidity used during EtO sterilization. The present invention seeks to overcome these problems by producing a low cost nonwoven laminate product comprising a novel co-extruded film adhesively bonded to a spunbond or other nonwoven substrate.

SUMMARY OF THE INVENTION

Nonwoven products of this invention are produced using a cast-lamination process. During cast lamination, a cast film is produced using conventional extrusion processes, such as co-extrusion. Multiple extruders are used to process and melt different polymers and then specially designed selector plugs and feed-blocks are used to combine the different polymers into different layers to form a multiple layer structure such as A-B, A-B-A, A-B-C, A-B-B-A, etc. The film is extruded from a wide die followed by cooling using a chill roll. After production, the cast film may further be embossed if needed. The cast film may also be wound on a roll for storage and/or transportation.

To form the composite nonwoven product of the invention, the cast film is laid upon and laminated to one or more nonwoven substrates on one or both sides of the film. A preferred lamination method uses pressure-sensitive adhesives (for example, hot melt, water based and solvent based adhesives). The adhesive is preferably applied using nozzles spraying fiberized adhesives. The fiber pattern can be chosen to optimize adhesion and softness or the ability to drape. Some representative examples of commercially available patterns include: Control Weave, Meltblown and UFD (Uniform fiber deposition). The number of holes per inch in the nozzle is chosen based on the intended end-use. Fiberization technologies suitable for use in this invention are available from companies like Nordson Corporation, Westlake, Ohio and Duluth, Ga. and Illinois Tool Works, Glenview, Ill. (See review, Cucuzza, C., "An Update on Hot Melt Adhesive Fiberization," Adhesives Age, 1994, Vol. 37, Issue 2, Argus Inc., Atlanta, Ga., pages 32-36. Other techniques for applying adhesive, such as gravure coating, slot coating and powder coating, may also be used. The adhesive is preferably applied to have a dry basis weight in the range of 1-10 gsm. If hot melt adhesives are used, the application temperature should not be so high as to damage the cast film. The completed composite nonwoven laminate may then be wound on a roll for storage and/or transportation. The foregoing cast-lamination process may be completed as a one-step process or may be broken into multiple separate steps.

The cast film preferably comprises multiple layers and is made from at least two polyolefinic resins, such as polyethylene resins, polypropylene homopolymers/copolymers, low density polyethylene (LDPE), linear low density polyethylene (LLPDE), ethyl vinyl acetate (EVA), ethylene methyl acrylate (EMA), maleic anhydride modified polyethylene (PE), amorphous polypropylene (PP), crystalline PP, random copolymers (RCP) of PP and PE, or blends thereof. Key properties in choosing suitable polymers are Melt Index, density and melting point. For polyethylene resins, the preferable melt index range is from 1-15 MFI. For polypropylene resins the preferable melt flow rate range is from 15-50 MFR. When producing a bi-laminate nonwoven product, the cast film should have at least two layers having different constituent parts (i.e., A-B). In the bi-laminate, the nonwoven substrate is in contact with and bonded to the A layer and when producing a tri-laminate nonwoven product, the cast film should have at least three layers of which at least two of the layers should have different constituent parts (i.e., A-B-A), where the A layers are in contact with and bonded to the nonwoven substrate. Other cast film structures, such as A-B-B-A, A-B-C, may be employed depending on the end use application. At least one layer should provide the barrier properties sufficient to prevent blood, viruses and bacteria from passing through; for example, the core layer (B) may comprise LDPE or a blend of LDPE and LLDPE for improved performance. It has been found that improvements in wet peel strength are realized when the A layer in contact with the nonwoven substrate comprises polypropylene homopolymer/copolymers and/or a blend of polypropylene with other polymers such as polyethylene. Preferred cast films have a basis weight in the range of 5-50 gsm and wherein the combined weight of said two outer layers lies between 3% and 90% of the total film weight in a ratio of outer layer to barrier layer to outer layer of from 1.5-97-1.5 to 45-10-45 by weight. The combined weight of said two outer layers preferably lies between 3% and 90% of the total film and the layers of the film do not have to be symmetrical. For example, in an A-B-A film, the ratio could be 3-90-7 by weight.

In preferred embodiments, the nonwoven substrate is a spunbond polypropylene substrate. However, substrates produced using other fibers such as PE, PET (polyester), bi-component fibers PE/PET may also be used. As used herein, a spunbond substrate is a nonwoven material constructed from small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 25 microns. Further, substrates produced using other nonwoven technologies, such as carding, hydro-entangling and wet-laid processes, may also be used to produce the nonwoven laminate product of this invention. Each nonwoven substrate should have a basis weight in the range of 10-100 gsm.

DETAILED ESCRIPTION OF INVENTION

Figure 1:
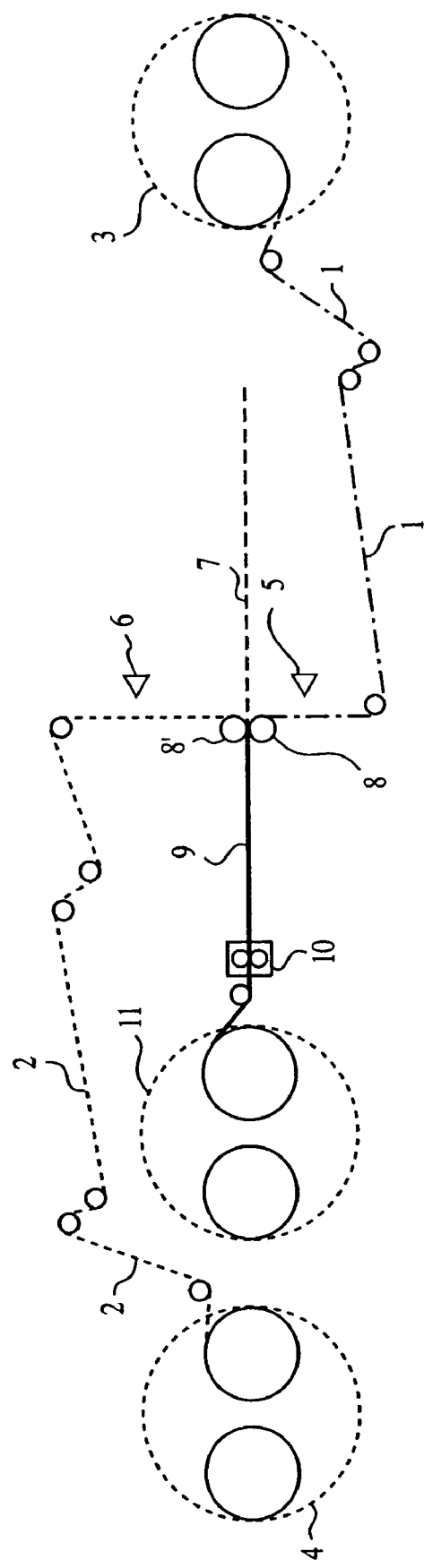
FIG. 1 is a schematic side elevation of an apparatus suitable for carrying out the process of the present invention.

More particularly, and referring now to FIG. 1, which outlines a general schematic for the cast lamination process which is suitable to produce an exemplary tri-laminate product according to the invention. One nonwoven fabric 1 is unwound from a primary nonwoven turret unwind 3 and a second nonwoven fabric 2 is unwound from a secondary nonwoven turret unwind 4. In the schematic illustrated in FIG. 1, turret winders and unwinds provide continuous operation. Adhesive applicators 5 and 6 then spray adhesive onto nonwoven fabrics 1 and 2. Cast co-extruded film 7 is then bonded to adhesive-coated, nonwoven fabrics 1 and 2 in lamination nip rolls 8, 8'. Cast film 7 can be produced in-line or unwound from a pre-made roll of film. The adhesive application can be done in one or more stages.

The term "nip" refers to doing lamination in multiple steps. Where the lamination is carried out in multiple stages, a bi-laminate is made in the first lamination step, and then the bi-laminate is converted into a tri-laminate in the second lamination step. Moreover, the adhesive can be applied onto the nonwoven fabric (substrate) or onto the film. The tri-laminate product 9 is edge trimmed and slit in edge trimmer 10. The exemplary tri-laminate product 10 is then wound up in a roll using turret rewind 11. To produce an exemplary bi-laminate product, one of the turret winders and one of the adhesive applicators would be eliminated.

Figure 2A:
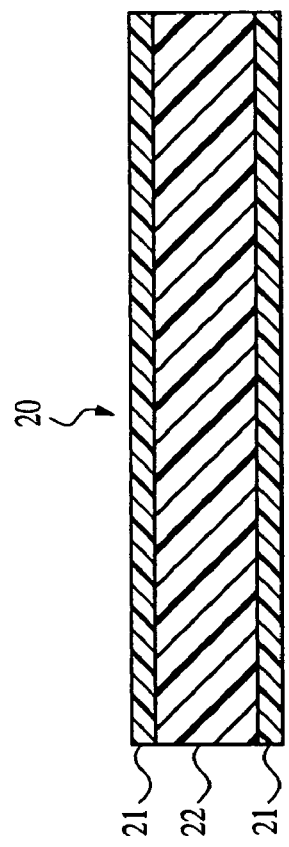
FIG. 2A is a schematic cross-section of the co-extruded film as described in Example 1.
Figure 2B:
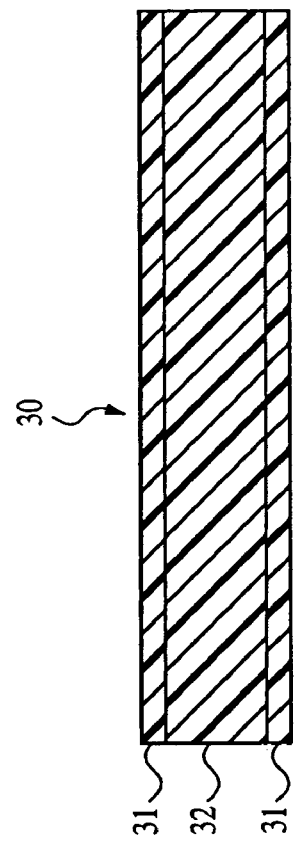
FIG. 2B is a schematic cross-section of the co-extruded film as described in Example 2.
Figure 2C:
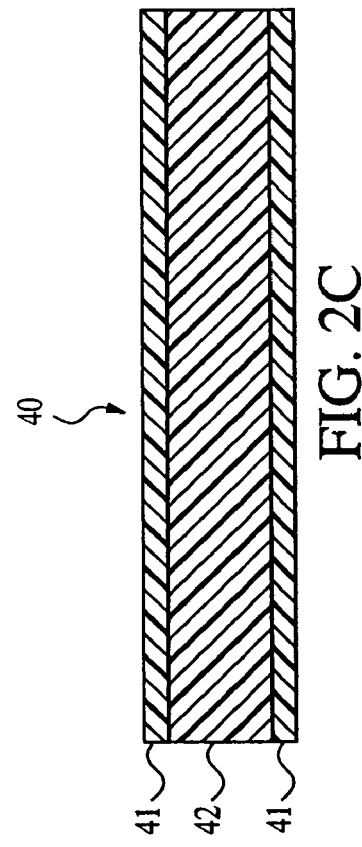
FIG. 2C is a schematic cross-section of the co-extruded film as described in Example 3.

FIG. 2A shows a schematic cross-section of one of the preferred constructions of the invention for co-extruded film, as described in additional detail in Example 1. In FIG. 2A, the outer layers 21 are blends of PP and PE while the core layer 22 is composed of an LDPE. FIG. 2B illustrates a schematic cross-section of the co-extruded film as described in Example 2. For the co-extruded film 30 drawn in FIG. 2B, the outer layers 31 and the core layer 32 are all composed of an LDPE. FIG. 2C shows a schematic cross-section of one of the preferred constructions for a co-extruded film 40, which is described in further detail in Example 3. The outer layers 41 are blends of PP and PE while the core layer 42 is a blend of LDPE and LLDPE. The cast film as illustrated in FIGS. 2A-2C can be made using the processes and equipment well known to those skilled in the art.

Figure 3:
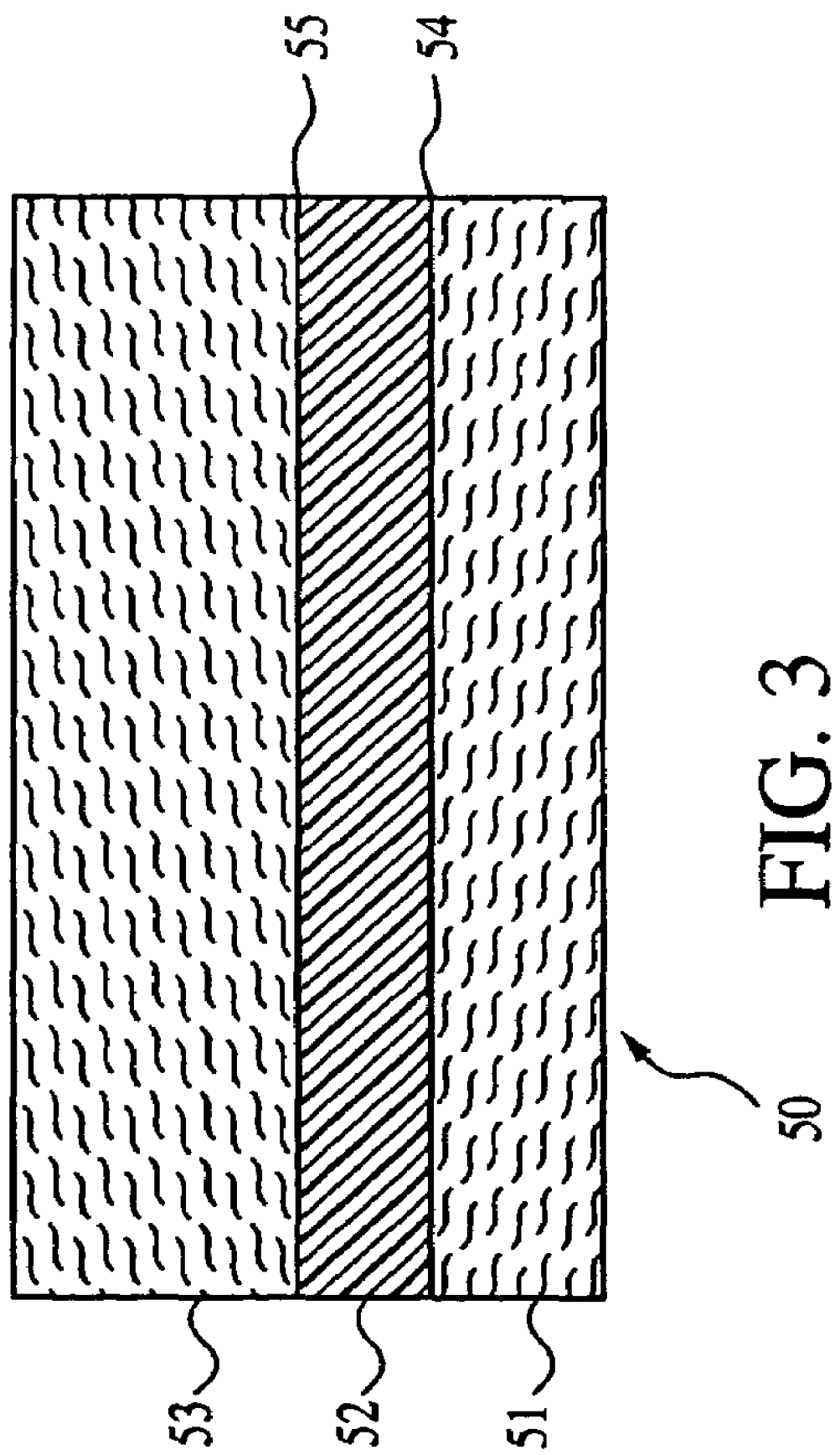
FIG. 3 is a schematic cross-section of a tri-laminate nonwoven product in accordance with the present invention.

FIG. 3 shows a schematic cross-section of a preferred tri-laminate composite nonwoven product 50 of the invention. The co-extruded film 52 forms the center of the laminate. The co-extruded film 52 is bonded to spunbond polypropylene (PP) inner layer 51 and spunbond polypropylene (PP) outer layer 53 using adhesives. The layers in the co-extruded film 52 are not shown in FIG. 3. Sample compositions of co-extruded film 52, including representation of the various layers in the cast film structure are shown in FIG. 2, as described above. The adhesive layers are too thin to be depicted in the schematic cross-section. However, the position of adhesive layer 54 is noted between inner layer 51 and co-extruded film 52, and the position of adhesive layer 55 is noted between outer layer 53 and co-extruded film 52.

Other objects and advantages of the present invention will become apparent from the following working examples.

EXAMPLE 1

A three layer (A-B-A) co-extruded film was produced. Core layer (B) was made from a LDPE (designated PE 1017). The linear low density polyethylene is commercially available from Chevron Phillips Chemical Company, The Woodlands, Tex. The nominal properties of PE 1017 resin (MSDS No. PL001) are a melt index of 7.0 gms/10 min (ASTM D1238-57T) and a density of 0.917 gms/cc (ASTM D1505-60T). It is characterized by excellent processability, high temperature stability and low neck-in. The color is translucent to clear.

The outer layers (A) were made using MARLEX EX01D resin, which is commercially available from Phillips Sumika Polypropylene Company (now Chevron Phillips Chemical Company, The Woodlands, Tex.). MARLEX EX01D is a blend of polypropylene and polyethylene (approximately 85% polypropylene and 15% polyethylene). Its nominal resin properties are density —0.906 g/cc (ASTM D1505); melt flow (230° C.)-35 g/10 min (ASTM D1238); melt point-167° C. (ASTM D3418); and crystallization temperature-110° C.

(ASTM D3418). To produce the co-extruded film of the above example, Marlex EX 01 D resin was fed from extruder A while LDPE 1017 was fed from extruder B. The two resins are then fed to a three layer feed-block and an ABA selector plug to produce the desired ABA co-ex film. Extruded ratio used in this particular example was 10-80-10 by weight.

Suitable equipment to produce co-extruded films is available from Cloeren Incorporated, Texas USA. Extruder A is a 2.5" size, 5 zone extruder with temperature profile from about 400° F. in first zone increasing to approximately about 555° F. in $5^{th}$ zone. Extruder B is a 3.5" size, 6 zone extruder with temperature profile of about 400° F. in first zone increasing to about 555° F. in $6^{th}$ zone. The die is maintained at approximately 555° F.

Each side of the cast film was laminated to a PP spunbond substrate using a hot melt adhesive designated Fuller NW 1023, which is commercially available from H.B. Fuller Company, St. Paul, Minn. The adhesive is applied in a fiberized spray pattern at processing temperature between 275 and 300° F. Line speed for the lamination process was about 300 fpm. This hot melt adhesive has the following nominal physical properties: Molten Gardner color-3; Mettler Soft. Point (ASTM D3461)-200° F.; specific gravity—0.96; viscosity at 275° F.-11,500 cP; viscosity at 300° F.-3,235 cP; viscosity at 325° F.-1,950 cP; and viscosity at 350° F.-1,250 cP.

The PP spunbond substrate laminated on one side of the cast film, preferably the outer layer, is a nominal 30 gsm "Ink Blue Polypropylene" designated "Grade 25224" manufactured by Ahlstrom Corp., Windsor Locks, Conn. This product is treated with a surfactant and an antistat to make it absorbent and have good static decay properties. However for the invention, repellent or absorbent substrates could be used, depending on the end use of the laminate. The basis weight is determined according to ASTM-D646-96. Other nominal properties include thickness at 0.63 psi-12 mils (ASTM D5729-97); grab tensile strength, MD-25 lbs, CD-14 lbs (ASTM D5034-95); elongation, MD-60%, CD-80% (ASTM D5034-95); and trapezoidal tear, MD-2.4 lb, CD-3.5 lb (ASTM D5733-95). The PP spunbond laminated on the other side of the cast film, preferably the inner layer, is Ahlstrom's nominal 20 gsm "Ink Blue Polypropylene" designated "Grade 25200". The basis weight is determined according to ASTM D 646-96. Other nominal properties include thickness at 0.63 psi-10 mils (ASTM D5729-97); grab tensile strength, MD-17 lbs, CD-10 lbs (ASTM D5034-95); elongation, MD-60%, CD-80% (ASTM D5034-95); and trapezoidal tear, MD-2.0 b, CD-3.0 lb (ASTM D5733-95).

EXAMPLE 2

As a comparative example, a three layer extruded film with each layer (A-A-A) comprising only Chevron's PE 1017 low-density polyethylene was laminated to the same PP spunbonds as in Example 1 with similar processing conditions. Each side of the cast film was laminated to a PP spunbond substrate using Fuller NW 1023 hot melt adhesive as in the previous example.

Properties of the constituent layers and the results of testing of both examples' wet/dry inner peel strength and blood barrier properties are shown in TABLE 1:

TABLE 1

| Date of Testing | Units | Example 1 | | | Example 2 | | |
| --- | --- | --- | --- | --- | --- | --- | --- |
| | | At Time of Production | After Aging (Approx. 1 month) | After EtO Sterilization | At Time of Production | After aging (Approx. 1 month) | After EtO Sterilization |
| Spunbond Weight (outer layer) | gsm | | 30 | | | 30 | |
| Spunbond Weight (inner layer) | gsm | | 20 | | | 20 | |
| Film Weight | gsm | | 18 | | | 18 | |
| Adhesive add-on (outer layer) | gsm | | 3 | | | 3 | |
| Adhesive add-on (inner layer) | gsm | | 2 | | | 2 | |
| Handelometer, MD | grams | | 89 | | | 86 | |
| Handelometer, CD | grams | | 41 | | | 47 | |
| Dry Inner Peel Strength (CD) | g/in | 81 | 137 | 157 | 74 | 138 | 108 |
| Wet Inner Peel Strength (CD) | g/in | 97 | 193 | 179 | 90 | 37 | 34 |
| Blood barrier (ASTM F 1670) | Pass/fail | pass | pass | pass | pass | pass | pass |

EXAMPLE 3

A three layer (A-B-A) co-extruded film was produced. Core layer (B) was made from a blend of a 30% LLDPE (designated MarFlex™ PE 7235) and 70% LDPE (designated PE 1017). The nominal properties of MarFlex™ PE 7235 resin are a hexane copolymer and commercially available from Chevron Phillips Chemical Company, The Woodlands, Tex. The nominal properties of MarFlex™ PE 7235 resin are a melt index of 3.5 gms/10 min (ASTM D1238E) and a density of 0.9235 gm/cc (ASTM D 1505). PE 1017 resin is described in Example 1. The blending is done in-line by using gravimetric feeders and the blend, along with other additives such as pigments, is then fed into the extruder B. The outer layers (A) were made using a polypropylene resin designated MARLEX EX01D resin as in Example 1.

To produce the co-extruded film of the above example, Marlex EX 01 D resin was fed from extruder A, while the blend of PE 7235 and LDPE 1017 resins was fed from extruder B. The two resin stocks are then fed to a three layer feed-block and an ABA selector plug to produce the desired ABA co-extruded film. Extruded ratio used in this particular example was 12.5-75-12.5 by weight.

Suitable equipment to produce co-ex films is available from Cloeren Incorporated, Texas USA. Extruder A is a 5 zone extruder with temperature profile from about 400° F. in first zone increasing to about 555° F. in $5^{th}$ zone. Extruder B is a 6 zone extruder with temperature profile of about 400° F. in first zone increasing to about 555° F. in $6^{th}$ zone. The die was maintained at approximately 555° F.

Each side of the cast film was laminated to a PP spunbond substrate using a hot melt adhesive designated Fuller HL 1713X ZP, which is commercially available from H.B. Fuller Company, St. Paul, Minn. This hot melt adhesive has the following nominal physical properties: 180 degree peel (60 sec/75F, 1 MIL)-6.7 lbs/inch, molten Gardner color-3; Mettler Soft. Point (ASTM D3461)-185° F.; viscosity at 250° F.-9,250 cp (mPa·s); viscosity at 275° F.-4,700 cP (mPa·s); viscosity at 300° F.-3,100 cP (mPa·s); viscosity at 325° F.-1,575 cP (mPa·s) and viscosity at 350° F.-1,050 cP (mPa·s). The SAFT (500 gms/in2 load) is 145° F. Fuller HL 1713X ZP adhesive is less viscous than Fuller NW 1023 used in the previous example. Line speed for the lamination process was about 300 fpm.

The PP spunbond substrate laminated on one side of the cast film is a nominal 30 gsm "Ink Blue Polypropylene" designated "Grade 25224" manufactured by Ahlstrom Corp., Windsor Locks, Conn. The PP spunbond laminated on the other side of the cast film is Ahlstrom's nominal 20 gsm "Ink Blue Polypropylene" designated "Grade 25200.

Properties of the constituent layers and the results of testing are shown in TABLE 2:

TABLE 2

| | | Example 3 | | |
|---|---|---|---|---|
| Date of Testing | Units | At Time of Production | After aging (Approx. 1 month) | After EtO Sterilization |
| Spunbond Weight (outer layer) | gsm | | 30 | |
| Spunbond Weight (inner layer) | gsm | | 20 | |
| Film Weight | gsm | | 18 | |
| Adhesive add-on (outer layer) | gsm | | 3 | |
| Adhesive add-on (inner layer) | gsm | | 2 | |
| Handelometer, MD | grams | | 87 | |
| Handelometer, CD | grams | | 44 | |
| Dry Inner Peel Strength (CD) | g/in | 83 | 178 | 260 |
| Wet Inner Peel Strength (CD) | g/in | 117 | 267 | 375 |
| Blood barrier (ASTM F 1670) | Pass/fail | pass | pass | pass |

As can be seen from TABLE 1 and 2, the wet peel strength of the Example 1 and 3 nonwoven laminate is significantly higher than the wet peel strength of the Example 2 fabric after aging and EtO sterilization. In order to obtain aging data, the samples are tested from the roll for peel strength. During EtO sterilization the samples are subjected to temperature and humidity as part of the sterilization cycle. It should also be noted that the softness and drape of the nonwoven laminates in these examples are better than commercially available nonwoven laminate used for medical applications. Fabric flexibility was measured by a Handleometer, Cat. 211-300 from Thwing Albert Instrument Co, 10960 Dutton Rd. Philadelphia, Pa. 19154 at a gap of 5 mm. Higher numbers correlate with less flexibility. The peel strength is measured using Ahistrom internal test method (No. TM 181). It uses a Zwick tensile tester (Model z 2.5, Zwick USA LP (Kennesaw, Atlanta, Ga.) to measure the force required to separate component layers of a laminate. Specimen size is 2"×6". The layers are separated manually for a distance of 1" and then mounted in the jaws. The crosshead speed is 12"/min. The average force to de-laminate is recorded. Peel strength in g/in is reported by dividing the average force by 2. For wet peel strength measurement the samples are soaked for approximately one minute and then the above procedure is repeated. The measurements and testing of the laminates as described herein are made by standardized methods well known to those skilled in the arts, as for example, those set forth in Ankuda et al, U.S. Pat. No. 6,638,605 B1, which is incorporated herein by reference in its entirety.

Although the invention has been described with reference to preferred embodiments, it will be appreciated by one of ordinary skill in the art that numerous modifications are possible in light of the above disclosure. For example, the nonwoven substrates, film weight/construction, adhesive application etc. may be modified as required for any particular application. All such variations and modifications are intended to be within the scope and spirit of this invention.

We claim:

1. A composite laminate comprising:
   a coextruded cast film layer, wherein said cast film layer comprises at least three layers having different constituent parts, wherein at least two layers of said cast film are outer layers, said outer layers consisting of a polypropylene resin selected from the group consisting of polypropylene homopolymers and polypropylene copolymers, and wherein at least one layer of said cast film layer is a barrier layer sufficient to prevent blood, viruses and bacteria from passing through the cast film layer, said barrier layer consisting of a member selected from the group consisting of low density polyethylene and a blend of low density polyethylene and a linear low density polyethylene; and
   at least two nonwoven substrate layers adhesively laminated to said outer layers,
   said composite laminate being characterized by its high wet peel strength, improved barrier properties and its being ethylene oxide sterilizable, the high wet peel strength not being diminished but enhanced on aging of the composite laminate.

2. The composite laminate according to claim 1, wherein said cast film layer has a basis weight in the range of 5 to 50 gsm.

3. The composite laminate of claim 1, wherein said nonwoven substrate layer comprises a spunbond polypropylene having a basis weight in the range of 10 to 100 gsm.

4. The composite laminate of claim 1, wherein said nonwoven substrate layer comprises a fabric having a basis weight in the range of 10 to 100 gsm and wherein said fabric is selected from the group consisting of polyethylene, polyester and bicomponent polyethylene/polyester fibers.

5. The composite laminate of claim 1, wherein said nonwoven substrate layer is laminated to said outer layer using an adhesive having a dry basis weight in the range of 1 to 10 gsm.

6. A composite laminate comprising:
a coextruded cast film layer, wherein said cast film layer comprises at least three layers, wherein at least two layers of said cast film are outer layers and have different constituent parts than the third layer, said outer layers consisting of a polypropylene resin selected from the group consisting of polypropylene homopolymers and polypropylene copolymers, and wherein at least one layer of said cast film is a barrier layer sufficient to prevent blood, viruses, and bacteria from passing through the cast film layer, said barrier layer consisting of a member selected from the group consisting of low density polyethylene and a blend of low density polyethylene and a linear low density polyethylene; and
at least two nonwoven substrate layers, each of which is adhesively laminated to one of said outer layers, wherein said nonwoven substrate layer comprises a fabric having a basis weight in the range of 10 to 100 gsm and wherein said fabric is selected from the group consisting of polypropylene, polyethylene, polyester and bicomponent polyethylene/polyester fibers,
said composite laminate being characterized by its high wet peel strength, improved barrier properties and its being ethylene oxide sterilizable, the high wet peel strength not being diminished but enhanced on aging of the composite laminate.

7. The composite laminate according to claim 6, wherein said cast film layer has three layers, a basis weight in the range of 5 to 50 gsm and wherein the combined weight of said two outer layers lies in the range of 3% to 90% of the total film weight.

8. A composite laminate comprising:
a coextruded cast film layer, wherein said cast film layer comprises at least three layers having different constituent parts, wherein at least two layers of said cast film are outer layers, said outer layers consisting of a member selected from the group consisting of polypropylene and blends of polyethylene and polypropylene, and wherein at least one layer of said cast film is a barrier layer sufficient to prevent blood, viruses and bacteria from passing through the cast film layer, said barrier layer consisting of linear low density polyethylene; and
at least two nonwoven substrate layers adhesively laminated to said outer layers,
said composite laminate being characterized by its high wet peel strengths of about 193 to about 267 after aging and about 179 to about 375 after EtO sterilization, improved barrier properties and its being ethylene oxide sterilizable, the high wet peel strength not being diminished but enhanced on aging of the composite laminate.

9. A composite laminate comprising:
a coextruded cast film layer, wherein said cast film layer comprises at least three layers having different constituent parts, wherein at least two layers of said cast film are outer layers, said outer layers consisting of a member selected from the group consisting of polypropylene and blends of polyethylene and polypropylene, and wherein at least one layer of said cast film is a barrier layer sufficient to prevent blood, viruses and bacteria from passing through the cast film layer, said barrier layer consisting of a blend of 30% linear low density polyethylene and 70% low density polyethylene; and
at least two nonwoven substrate layers adhesively laminated to said outer layers, said composite laminate being characterized by its high wet peel strengths of about 267 after aging and about 375 after EtO sterilization, improved barrier properties and its being ethylene oxide sterilizable, the high wet peel strength not being diminished but enhanced on aging of the composite laminate.

* * * * *

UNITED STATES PATENT AND TRADEMARK OFFICE
CERTIFICATE OF CORRECTION

| | |
|---|---|
| PATENT NO. | : 7,501,363 B2 |
| APPLICATION NO. | : 10/535498 |
| DATED | : March 10, 2009 |
| INVENTOR(S) | : Rahul K. Dharmadhikary et al. |

It is certified that error appears in the above-identified patent and that said Letters Patent is hereby corrected as shown below:

In "(73) Assignee:," delete "The Boeing Company, Chicago, IL" and insert

--Ahlstrom Windsor Locks LLC, Windsor Locks, CT--.

Signed and Sealed this

Twenty-fourth Day of November, 2009

David J. Kappos
*Director of the United States Patent and Trademark Office*